US00PP25454P3

(12) United States Plant Patent
Esselen

(10) Patent No.: US PP25,454 P3
(45) Date of Patent: Apr. 21, 2015

(54) GRAPEFRUIT TREE NAMED 'JR13'

(50) Latin Name: *Citrus×paradisi*
Varietal Denomination: JR13

(76) Inventor: Leon Esselen, Malelane (ZA)

( * ) Notice: Subject to any disclaimer, the term of this patent is extended or adjusted under 35 U.S.C. 154(b) by 47 days.

(21) Appl. No.: 13/507,378

(22) Filed: Jun. 22, 2012

(65) Prior Publication Data

US 2013/0347155 P1 Dec. 26, 2013

(51) Int. Cl.
*A01H 5/00* (2006.01)

(52) U.S. Cl.
USPC ..... Plt./201

(58) Field of Classification Search
USPC ..... Plt./201
See application file for complete search history.

*Primary Examiner* — Kent L Bell
(74) *Attorney, Agent, or Firm* — Michelle Bos

(57) ABSTRACT

'JR13' is a new and distinct grapefruit tree notable for its attractive, seedless fruit.

1 Drawing Sheet

Genus and species: *Citrus×paradisi.*
Variety denomination: 'JR13'.

BACKGROUND AND SUMMARY OF THE VARIETY

The new grapefruit variety 'JR13' originated in Malelane, South Africa in 2005 as an induced mutation of 'FE1' grapefruit (not patented). Mutation was induced through exposure of budwood to gamma radiation. Radiated budwood was budded to 'Carrizo' citrange rootstock and the scion selections monitored for characteristics of low seed content. The selection with the lowest seed count, highest fruit yield, and best internal fruit quality was selected for planting and further observation at Malelane, South Africa and named 'JR13'. 'JR13' has been observed over successive generations and has been found to retain its distinguishing characteristics.

'JR13' is a new and distinct grapefruit tree notable primarily for its attractive, seedless fruit. Table 1 shows a comparison of 'JR13' to parent 'FE1' and 'Marsh' (not patented) grapefruit varieties.

TABLE 1

Comparison of 'JR13' to Known Varieties

| Characteristic | 'JR13' | 'FE1' | 'Marsh' |
|---|---|---|---|
| Seed quantity | Seedless | Some seeds | Some seeds |
| Maturity | Mid- to late-season | Mid-season | Early season |
| Fruit shape | Oval to globose | Globose | Globose |

BRIEF DESCRIPTION OF THE PHOTOGRAPHS

FIG. 1 shows whole and sectioned fruit of the 'JR13' grapefruit tree.

Because lighting conditions can affect the colors shown in photographic illustrations, color characteristics of this new variety should be determined with reference to the observations described herein, rather than from the illustrations alone.

DETAILED BOTANICAL DESCRIPTION

The following detailed botanical description is based on observations of trees and fruit of 'JR13', budded to 'Carrizo' citrange rootstock and planted in 2010. Observations were recorded and photographs taken during the 2011 and 2014 growing seasons at Malelane, South Africa. It should be understood that the characteristics described will vary somewhat depending upon cultural practices and climatic conditions, and can vary with location and season. Quantified measurements are expressed as an average of measurements taken from a number of individual trees of the new variety. The measurements of any individual tree, or any group of trees, of the new variety may vary from the stated average. Color references are to The Royal Horticultural Society Colour Chart Tree:
- *Vigor.*—Moderate.
- *Density of canopy.*—Dense.
- *Habit.*—Compact growth habit.
- *Height.*—1.60 m.
- *Spread.*—2.6 m.
- *Trunk diameter* (*at* 30 *cm above the graft*).—18 cm.
- *Bark texture.*—Smooth.
- *Bark color.*—Grey-brown 199C.
- *Tendency toward alternate bearing.*—No.
- *Hardiness zone.*—9 and 10.

Branch (fruiting branches located at around 1 m above the graft union):
- *Length.*—25 cm.
- *Diameter.*—2.8 cm.
- *Crotch angle.*—25-30°.
- *Internode length.*—3 cm.
- *Bark color.*—Mature branches grey-brown 199C.
- *Bark texture.*—Smooth.
- *Thorns present?.*—Yes.
- *Thorn length.*—10 mm.
- *Current year shoot length.*—30 cm.
- *Current year shoot color.*—Green N137C.

Flower buds:
- *Shape.*—Cylindrical to oblate.
- *Length.*—14 to 16 mm.
- *Diameter.*—4 to 6 mm.
- *Color.*—Green-white 157C.

Flowers:
- *Flowering period.*—10 to 16 days, late August, early September in Malelane, South Africa.

*Quantity per node.*—9 to 14.
*Diameter.*—23 to 26 mm.
*Depth.*—16 to 18 mm.
*Fragrance.*—Aromatic, sweet.
*Petals.*—5 per flower.
*Petal shape.*—Elongated, apex acute.
*Petal margin.*—Undulating.
*Petal width.*—4 to 5 mm.
*Petal length.*—17 to 18 mm.
*Petal color.*—Upper surface white 155A, lower surface yellow-white 158A.
*Sepal.*—Length 5.4 mm, width 4.6 mm, acuminate tip; upper surface yellow-green 149D, lower surface yellow-green 149B.
*Pedicel.*—Length 9 mm, green 138B.
*Pistil.*—Single, length 13 mm, yellow-green 154D.
*Style.*—Single, length 9 to 10 mm, white NN155C.
*Stigma.*—Yellow-green 151B.
*Ovary.*—Ovate, yellow-green 151A.
*Stamen.*—40 to 50 per flower, length 17 mm.
*Filament.*—Straight, length 11 to 12 mm.
*Anther.*—Antrorse, length 4 to 6 mm, yellow 4A.
*Pollen.*—Yellow 2A, profuse.

Leaves:
*Length.*—11 cm.
*Width.*—7 cm.
*Length:width ratio.*—1:0.6.
*Blade margin.*—Smooth.
*Leaf shape.*—Oval.
*Apex shape.*—Acute.
*Base.*—Marginally developed to well defined leaf wing.
*Color of upper surface.*—Green 141A.
*Color of lower surface.*—Yellow-green 146B.
*Leaf texture.*—Smooth.
*Petiole length.*—21.3 mm.
*Petiole diameter.*—17.7 mm.
*Petiole color.*—Green 141C.
*Wings present?.*—Yes.
*Wing width.*—9 mm.

Fruit:
*Quantity per cluster.*—1 to 7.
*Axial diameter.*—77.2 mm.
*Apical diameter.*—78.8 mm.
*Weight.*—259 g.
*General shape in profile.*—Oval to globose.
*Navel.*—Absent.
*Rind color.*—Yellow 11A.
*Oil glands per cm$^2$.*—19.
*Oil gland diameter.*—1.3 mm.
*Rind thickness.*—5.5 mm.
*Ease of peeling.*—Difficult.
*Rind texture.*—Smooth.
*Albedo thickness.*—3.1 mm.
*Albedo color.*—White NN155C.
*Quantity of fruit segments per fruit.*—12.
*Segment length.*—71 mm.
*Segment width.*—20 mm.
*Toughness of segment membrane.*—Moderate.
*Juice sac length.*—19.8 mm.
*Juice sac shape.*—Elongated.
*Juice sac length to width ratio.*—1:6.6.
*Juice sac color.*—Yellow 2B.
*Juice soluble solids (° brix).*—13.1.
*Relative harvest maturity.*—Mid- to late-season; 4$^{th}$ week of May in Mpumalanga Province, South Africa.
*Harvest window.*—4 weeks.
*Seeds present.*—None.
*Stem length.*—3-4 cm.
*Stem diameter.*—3.3 mm.
*Stem color.*—Green 146B.

Market use: Fresh, juice and segments.
Keeping quality: Good.
Shipping quality: Good.
Disease/pest resistance/susceptibility: None noted.

The invention claimed is:

1. A new and distinct variety of grapefruit tree, substantially as illustrated and described herein.

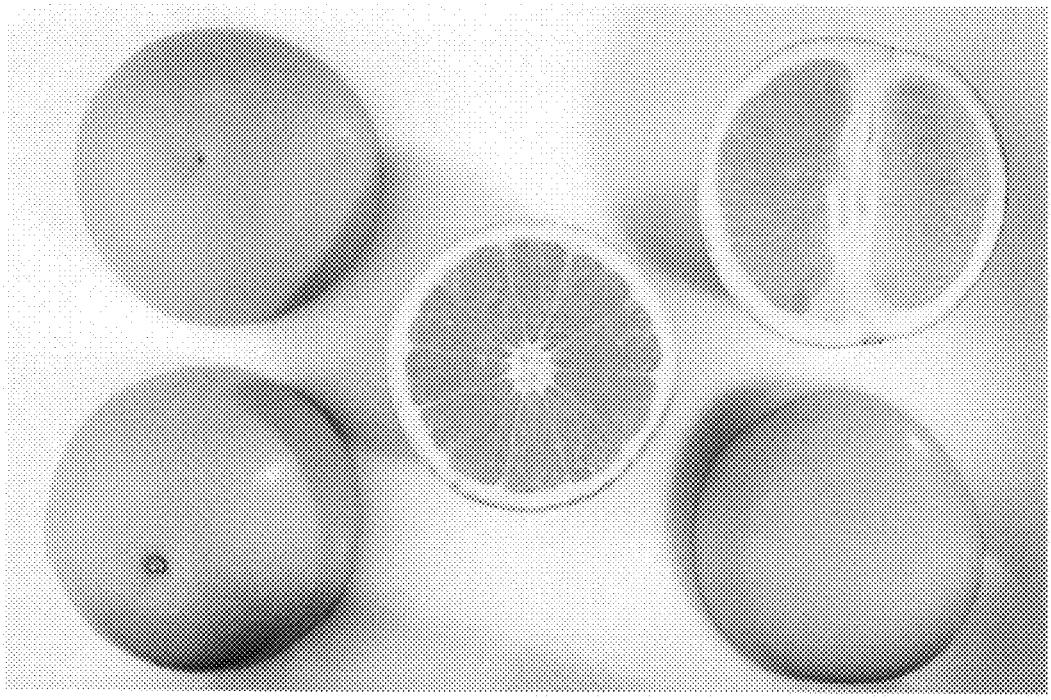

* * * * *